(12) United States Patent
Eckhouse et al.

(10) Patent No.: US 8,758,364 B2
(45) Date of Patent: Jun. 24, 2014

(54) DEVICE AND METHOD FOR CLOT ENGAGEMENT AND CAPTURE

(75) Inventors: Ronen Eckhouse, Shimshit (IL); Yuri Sudin, Modiin (IL); Shimon Eckhouse, Haifa (IL)

(73) Assignee: Rapid Medical Ltd. (IL)

( * ) Notice: Subject to any disclaimer, the term of this patent is extended or adjusted under 35 U.S.C. 154(b) by 3 days.

(21) Appl. No.: 13/279,870

(22) Filed: Oct. 24, 2011

(65) Prior Publication Data

US 2012/0041449 A1    Feb. 16, 2012

Related U.S. Application Data

(63) Continuation-in-part of application No. 13/059,319, filed as application No. PCT/IL2009/000834 on Aug. 30, 2009.

(60) Provisional application No. 61/119,369, filed on Dec. 2, 2008, provisional application No. 61/093,173, filed on Aug. 29, 2008.

(51) Int. Cl.
*A61B 17/22* (2006.01)

(52) U.S. Cl.
USPC .......................................................... 606/127

(58) Field of Classification Search
USPC .................. 606/127, 200, 159, 128, 113, 114
See application file for complete search history.

(56) References Cited

U.S. PATENT DOCUMENTS

| | | | |
|---|---|---|---|
| 3,367,101 A | 2/1968 | Garner et al. | |
| 3,435,826 A | 4/1969 | Fogarty | |
| 4,030,503 A | 6/1977 | Clark, III | |
| 4,403,612 A | 9/1983 | Fogarty | |
| 4,706,671 A | 11/1987 | Weinrib | |
| 4,762,130 A | 8/1988 | Fogarty et al. | |
| 4,890,611 A | 1/1990 | Monfort et al. | |
| 5,011,488 A | 4/1991 | Ginsburg | |
| 5,112,347 A | 5/1992 | Taheri | |
| 5,192,286 A | 3/1993 | Phan et al. | |
| 5,411,509 A | 5/1995 | Hilal | |
| 5,490,859 A | 2/1996 | Mische et al. | |

(Continued)

FOREIGN PATENT DOCUMENTS

| | | |
|---|---|---|
| EP | 0 820 729 A1 | 1/1998 |
| EP | 1 949 921 A2 | 7/2008 |

(Continued)

OTHER PUBLICATIONS

International Search Report for PCT/IL2009/000834, mailed Apr. 9, 2010, corresponding to U.S. Appl. No. 13/059,318 (5 pages total).

(Continued)

*Primary Examiner* — Tuan V Nguyen
*Assistant Examiner* — Tin Nguyen
(74) *Attorney, Agent, or Firm* — Finnegan, Henderson, Farabow, Garrett & Dunner, LLP

(57) ABSTRACT

A clot removal device and method for removing a clot from a blood vessel may include an expandable clot engagement element, an expandable clot capture element, and a sheath surrounding and compressing the capture element and the engagement element. The sheath may be removable to thereby enable the capture element to expand in a blood vessel in which the sheath is deployed, and to enable the engagement element to expand within the capture element.

14 Claims, 10 Drawing Sheets

(56) References Cited

U.S. PATENT DOCUMENTS

| | | | |
|---|---|---|---|
| 5,695,519 | A | 12/1997 | Summers et al. |
| 5,772,674 | A | 6/1998 | Nakhjavan |
| 5,895,398 | A * | 4/1999 | Wensel et al. ............ 606/159 |
| 6,096,053 | A | 8/2000 | Bates |
| 6,159,230 | A | 12/2000 | Samuels |
| 6,695,858 | B1 | 2/2004 | Dubrul et al. |
| 6,902,540 | B2 | 6/2005 | Dorros et al. |
| 7,326,220 | B1 | 2/2008 | Goldstein |
| 8,123,769 | B2 * | 2/2012 | Osborne ..................... 606/159 |
| 8,298,244 | B2 * | 10/2012 | Garcia et al. ............... 606/127 |
| 2001/0031980 | A1 | 10/2001 | Wensel et al. |
| 2002/0095169 | A1 | 7/2002 | Maitland et al. |
| 2002/0123765 | A1 | 9/2002 | Sepetka et al. |
| 2002/0161397 | A1 | 10/2002 | Mathews et al. |
| 2003/0191492 | A1 | 10/2003 | Gellman et al. |
| 2003/0236534 | A1 | 12/2003 | Kayan |
| 2005/0154400 | A1 | 7/2005 | Kato et al. |
| 2005/0228417 | A1 | 10/2005 | Teitelbaum et al. |
| 2006/0195137 | A1 * | 8/2006 | Sepetka et al. ............. 606/200 |
| 2007/0185501 | A1 | 8/2007 | Martin et al. |
| 2007/0208370 | A1 | 9/2007 | Hauser et al. |

FOREIGN PATENT DOCUMENTS

| | | |
|---|---|---|
| WO | WO 99/23952 | 5/1999 |
| WO | WO 99/60933 | 12/1999 |
| WO | WO 2008/057554 A1 | 5/2008 |
| WO | WO 2010/046897 A1 | 4/2010 |

OTHER PUBLICATIONS

International Search Report for PCT/IL2009/000992, mailed Mar. 4, 2010, corresponding to U.S. Appl. No. 13/125,324 (5 pages total).

USPTO Office Action mailed Jun. 11, 2013, for U.S. Appl. No. 13/279,880, (7 pages total).

USPTO Office Action mailed Apr. 23, 2013, for U.S. Appl. No. 13/125,324 (27 pages total).

Communication from European Patent Office in European Appl. EP 09 764 899 dated Aug. 22, 2012, corresponding to U.S. Appl. No. 13/125,324 (3 pages).

Communication from European Patent Office in European Appl. EP 10 191 770 dated Feb. 10, 2011, corresponding to U.S. Appl. No. 13/059,318 (4 pages total).

USPTO Final Office Action mailed Sep. 30, 2013, for U.S. Appl. No. 13/279,880, (8 pages total).

* cited by examiner

DEVICE AND METHOD FOR CLOT ENGAGEMENT AND CAPTURE

CROSS-REFERENCE TO RELATED APPLICATION

This patent application is a continuation-in-part of U.S. patent application Ser. No. 13/059,319, filed on Feb. 16, 2011, entitled EMBOLECTOMY DEVICE, which is a 35 U.S.C. §371 of PCT/IL09/00834, filed on Aug. 30, 2009, which claims the benefits of priority under 35 U.S.C. §§119-120 to U.S. Provisional Application 61/119,369, filed on Dec. 2, 2008, and to U.S. Provisional Application 61/093,173, filed on Aug. 29, 2008, the entire disclosure of which is incorporated herein by reference.

TECHNICAL FIELD

Embodiments of the present disclosure generally relate to devices and methods for treating occlusions within vasculature. More particularly, embodiments of the present disclosure relate to devices and methods for removal of clots (e.g., emboli and thrombi) found in blood vessels, among other things.

TECHNICAL BACKGROUND

Blood clots (e.g., emboli and thrombi) are examples of blockages that may form in mammalian blood vessels. A clot in an individual's blood vessel may become dangerous when it restricts blood flow, thereby placing the individual at risk for medical traumas, such as a stroke or a heart attack. Therefore, there may be a need to remove clots that are lodged within blood vessels.

A variety of devices and procedures have been used to remove clots from blood vessels. For example, a catheter with a balloon on its distal tip may be inserted into a blood vessel and passed through the clot, after which the balloon is inflated. The balloon may then be withdrawn from the blood vessel to remove the clot.

Another example of a clot removal device is a catheter containing a spiral section at its distal end. The catheter with spiral section may be delivered to a clot site within a blood vessel, and the spiral section may then be used to cut into the clot. The spiral section, therefore, may grasp to an inner portion of the clot prior to withdrawing the clot from the blood vessel.

One risk that exists with clot removal devices is that a piece of the clot may break away during the removal process, travel through the vasculature, and cause traumatic damage. This may occur for various reasons. For example, if the clot removal device passes through the clot prior to deployment, the pre-deployment activity can disrupt the clot, causing pieces to break away. Further, there is an increased risk of deploying a device in uninvolved distal territory. There is a need for devices and methods that may allow a clot to be removed from a blood vessel, while reducing the risk that a clot or portion of a clot may become dislodged during the removal process, causing further risk to the patient.

SUMMARY OF A FEW EXEMPLARY EMBODIMENTS

Embodiments of the present disclosure provide devices and methods for removing clots from blood vessels.

An aspect of the present disclosure includes a clot removal device with an expandable clot engagement element, an expandable clot capture element, and a sheath surrounding and compressing the capture element and the engagement element. The sheath may be removable to thereby enable the capture element to expand in a blood vessel in which the sheath is deployed, and to enable the engagement element to expand within the capture element.

In various embodiments, the clot removal device may include one or more of the following features: the capture element may surround the engagement element; the engagement element may be a coil; the capture element may include a mesh-like structure; the engagement element may be sized to be movable within the capture element upon removal of the sheath; the engagement element may be sized to be rotatable within the capture element upon removal of the sheath; the capture element may have a length that may be longer than a length of the engagement element; there may be a locking mechanism for locking the clot engagement element within the clot capture element; the capture element may be sized so that in a deployed state it engages a blood vessel wall, and the engagement element may be sized so that in a deployed state the engagement element may be movable within the capture element; and the capture element and the engagement element may be configured such that during use, the engagement element may be between the capture element and the clot.

In another aspect, a method of removing a clot from a blood vessel may include deploying a clot removal device in a blood vessel at a clot site. The clot removal device may include an expandable clot engagement element, an expandable clot capture element, and a sheath surrounding and compressing the capture element and the engagement element. The method may further include removing the sheath from the capture element and the engagement element such that the capture element may expand within the blood vessel, and the engagement element may expand within the capture element. A locking device may be used to lock the clot engagement element within the clot capture element. Additionally, the capture element may engage the blood vessel wall in a deployed state, and the engagement element may move within the capture element in the deployed state. Further, when the capture element and the engagement element may be deployed, the engagement element may be between the capture element and the clot.

Additional aspects of the disclosure will be set forth in part in the description which follows, and in part will be readily ascertainable from the description, or may be learned by practice of the disclosure.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the disclosure and together with the description, serve to explain the principles of the disclosure.

DESCRIPTION OF THE EMBODIMENTS

Reference will now be made in detail to exemplary embodiments of the present disclosure, examples of which are illustrated in the accompanying drawings. Wherever possible, the same reference numbers will be used throughout the drawings to refer to the same or like parts.

Embodiments of the present disclosure relate generally to medical devices and methods for treating occlusions in a body. More particularly, embodiments of the present disclosure relate to devices and method for removing clots, including, but not limited to, emboli and thrombi from blood vessels. It should be emphasized, however, that embodiments of the present disclosure may also be utilized in other medical procedures where removal of a blockage or a foreign body is desired.

In accordance with embodiments of the disclosure, there may be provided a clot removal device including an expandable clot engagement element. An expandable clot engagement element may be any structure that, upon deployment in a blood vessel, may be able to grip, grasp, circumscribe, or retain and/or retrieve a blood clot or other obstruction.

Figure 1A:
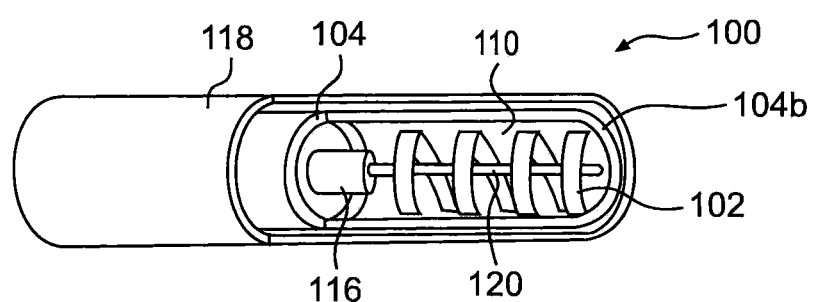
FIG. 1A is a sectional view of a medical device for removing a clot from a blood vessel, consistent with an embodiment of the disclosure.

FIG. 1A illustrates one example of a clot engagement element 102, in connection with exemplary clot removal device 100. For purposes of this disclosure, "proximal" refers to the end closer to the device operator during use, and "distal" refers to the end further from the device operator during use.

Figure 1B:
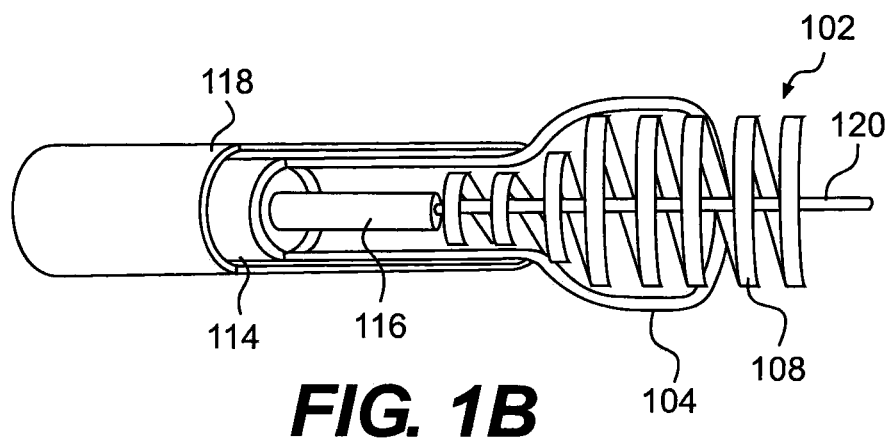
FIGS. 1B and 1C are a sectional views of a the medical device of FIG. 1A in expanded configurations.
Figure 7A:
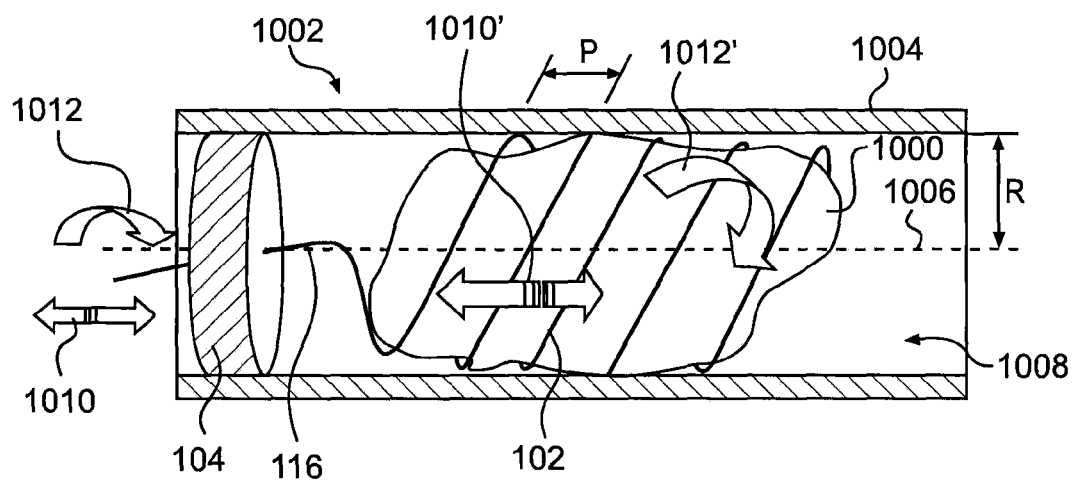
FIGS. 7A-7B are sectional views of the body portion of FIGS. 6A-6B showing movement of a clot engagement element during a method of removing a clot from the body portion, using the medical device of FIG. 1A.

As illustrated in FIG. 1B, in one embodiment, clot engagement element 102 may include a coil with one or more windings 108. The windings 108 may be angled relative to a longitudinal axis 1006 of a blood vessel 1002 (FIG. 7A). The angle of the windings 108 may range from approximately 0 degrees to approximately 180 degrees, and more preferably from approximately 90 degrees to approximately 180 degrees.

Figure 6A:
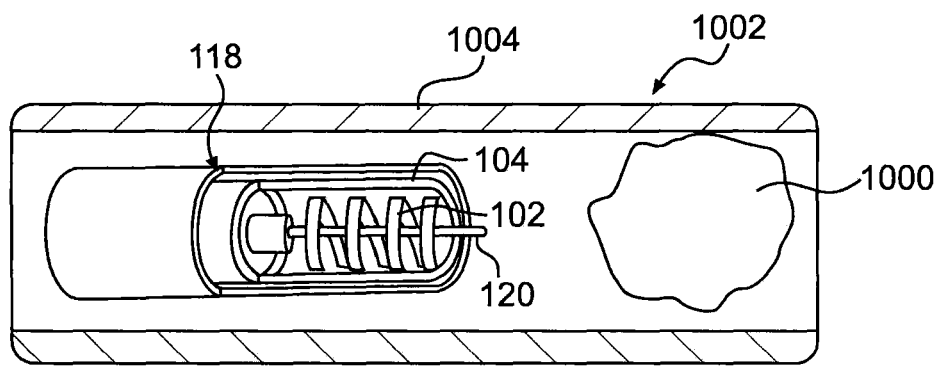
FIG. 6A-6B are sectional views of a body portion showing steps of a method of removing a clot from the body portion, using the medical device of FIG. 1A.
Figure 6B:
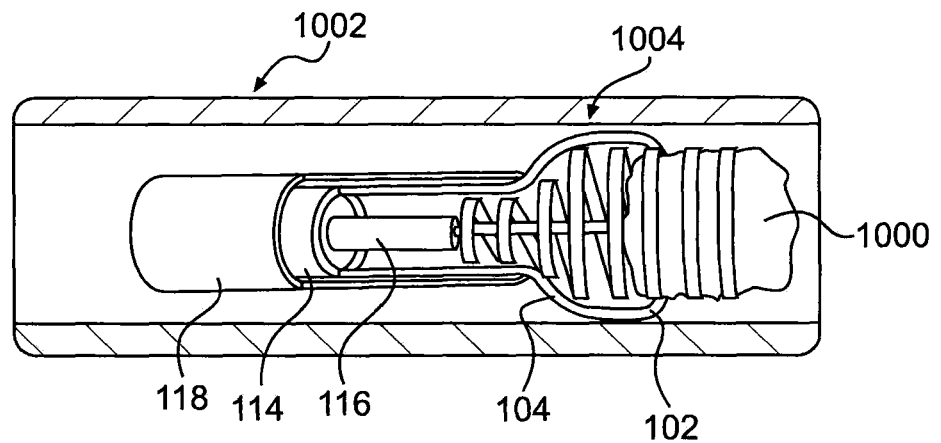

A plurality of windings 108 may further form a helical configuration, whereby the plurality of windings 108 share a substantially constant pitch P and/or a substantially constant radius R, as illustrated with reference lines in FIG. 7A. Thus, during rotation, adjacent windings having the same radius and pitch will follow substantially the same path of rotation. Alternatively, the one or more windings 108 may includes a varied pitch and/or a varied radius. The one or more windings 108 may be any shape and/or configuration such that they may be configured to rotate about a clot lodged within a blood vessel, to grasp at least a portion of the outer circumference of the clot, and to separate the clot from the blood vessel (FIG. 6B). For example, the one or more windings 108 may be wound in any suitable shape, including, but not limited to a circle and an oval. The one or more windings 108 may also be a continuous piece of material. The continuous piece of material may have any suitable cross-sectional shape, including, but not limited to, a circle, an oval, a polygon, or any other shape that is capable of being wound.

The one or more windings 108 may further include an atraumatic bottom, clot contacting surface that may be substantially flat or rounded. The bottom, clot contacting surface of the one or more windings 108 may mitigate the tendency of a clot 1000 to break into multiple pieces upon contact. Further, the bottom, clot contacting surface of the one or more windings 108 may be textured for enhanced gripping of a clot 1000. A top, exterior surface of the one or more windings 108 may also be an atraumatic surface. The atraumatic top, exterior surface of the one or more windings 108 may mitigate damage to tissue that the one or more windings 108 may contact at a clot site. Windings 108 may also include a coating on their top and/or bottom surfaces. The coating may include, but is not limited to, a lubricant and/or an anesthetic.

Clot engagement element 102 may further be a spring-like member configured to self-expand and retract. Expansion and retraction may be in longitudinal and/or radial directions. Accordingly, clot engagement element 102 may include a contracted configuration (FIG. 1A) and an expanded configuration (FIG. 1B). The contracted configuration may be maintained when a sheath 118 substantially surrounds an outer surface of clot engagement element 102. The expanded configuration may be achieved when sheath 118 is removed from at least a portion of the outer surface of clot engagement element 102 (Sheath 118 will be discussed in further detail below).

Clot engagement element 102 may be configured to expand to approximately an inner diameter of a blood vessel 1002 (FIG. 7A). Expansion to approximately an inner diameter of blood vessel 1002 may result (but not necessarily result) in clot engagement element 102 exerting a force on a wall 1004 of blood vessel 1002. If a force is exerted on the vessel wall 1004, the force may result in separation of a clot 1000 from wall 1004 of blood vessel 1002. The resulting separation may be beneficial because in many instances, clot 1000 may be lodged in blood vessel 1002. Accordingly, separation of clot 1000 from wall 1004 of blood vessel may reduce the amount of force required to further remove clot 1000 from blood vessel 1002 and mitigate the tendency of clot 1000 to break into multiple fragments during removal from blood vessel 1002.

A shaft 116 may extend from a proximal end of clot engagement element 102. Shaft 116 may be an elongate member configured to control rotational and longitudinal movement of clot engagement element 102. For example, as illustrated in FIG. 7A, movement of shaft 116 in the directions shown by arrow 1010 may cause movement of clot engagement element 102 in the directions of arrow 1010'. Further, rotation of shaft 116 in the direction of arrow 1012 may cause rotational movement of clot engagement element 102 in the direction of arrow 1012'.

Shaft 116 may have any shape and/or configuration so long as shaft 116 may be configured to rotate and advance clot engaging element 102. Further, shaft 116 may have any suitable cross-sectional shape so long as shaft 116 may be configured to rotate. (FIG. 7A).

While the foregoing described embodiment presents an example of clot engagement element 102 as a wound structure, in a broader sense, the clot engagement element may have any shape and/or configuration so long as it is capable of grasping and removing a clot from a blood vessel. Further, the clot engagement element may be any size such that it is capable of traversing a lumen of a blood vessel.

The clot engagement element may be constructed of any suitable biocompatible material having sufficient flexibility and/or rigidity to traverse the lumen of the blood vessel. Biocompatible materials may include, but are not limited to, synthetic plastics, stainless steel, ePTFE, PTFE, metal-polymer composites, and metal alloys of nickel, titanium, nickel-titanium, copper cobalt, chromium, and iron.

In broader embodiments of the disclosure, a clot engagement element may include any structure or mechanism capable of engaging with a clot or other obstruction. For example, a clot engaging element may include one or more hooks, forceps, expandable cages, expandable balloons, or thermal or chemical mechanisms for causing a mechanical structure to connect with a clot or obstruction.

In accordance with at least some embodiments of the disclosure, there may be provided an expandable clot capture element. An expandable clot engagement element may be any structure that, upon deployment in a blood vessel, is able to capture a clot that has been engaged by a clot engaging element.

Consistent with an exemplary embodiment of the disclosure, an exemplary clot capture element 104 is illustrated in FIG. 1. The clot capture element 104 may be constructed to enable clot engagement element 102 to be movable therein upon deployment in a blood vessel. For example, upon removal of sheath 118 as will be described later in greater detail, clot engagement element 102 may be configured to rotate, expand, and/or longitudinally slide within clot capture element 104.

Figure 1C:
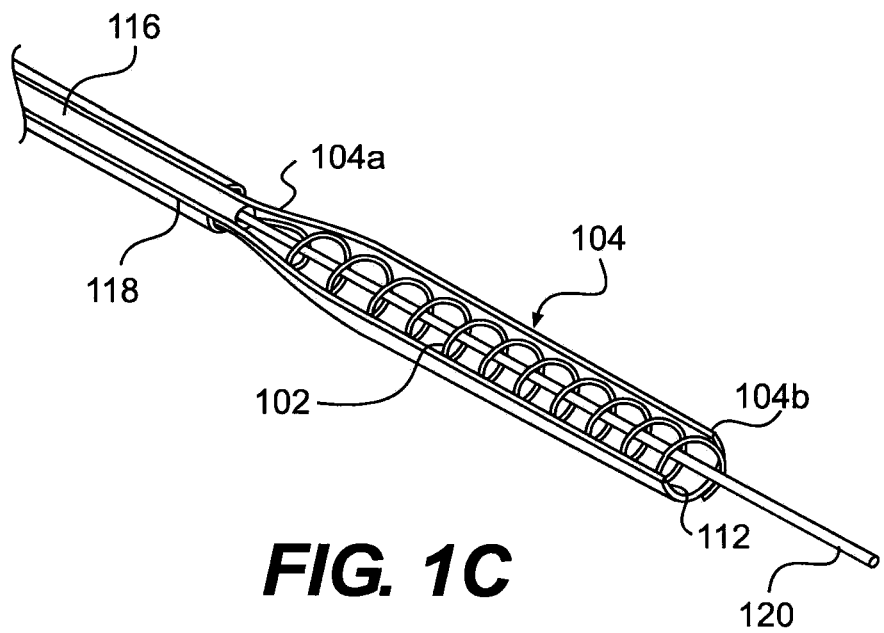

As illustrated in FIG. 1C, clot capture element 104 may include, but is not limited to, a catheter having a proximal end 104a and a distal end 104b. Proximal and distal ends 104a, 104b may each include an opening therein 112. Opening 112 at proximal and distal ends 104a, 104b may be in communication with a central lumen 110 in clot capture element 104 (FIG. 1A). Central lumen 110 in clot capture element 104 may allow for insertion of clot engagement element 102, as well as other components that may aid in a medical procedure, including, but not limited to, an optional guidewire 120, vacuum source, illumination and/or imagining devices, and tools for grasping a clot.

Clot capture element 104 may further be configured to expand and contract. Accordingly, clot capture element 104 may be configured to transition between a contracted configuration (FIG. 1A) and an expanded configuration (FIG. 1B), in a spring-like manner, in response to movement relative to a surrounding sheath 118. Similar to clot engagement element 102, clot capture element 104 may be configured to expand to a size that is substantially the same as an inner diameter of blood vessel 1002 at a clot site. The expansion of clot capture element 104 to the inner diameter of blood vessel 1002 and exerted force on blood vessel wall 1004 at the clot site may aid in separating a clot 1000 from a wall 1004 of blood vessel 1002. The separation may result in a reduction of the required force to remove clot 1000 from blood vessel 1002. The separation may also aid in mitigating the tendency of clot 1000 to break into multiple pieces during removal of clot 1000 from blood vessel 1002.

Figure 2:
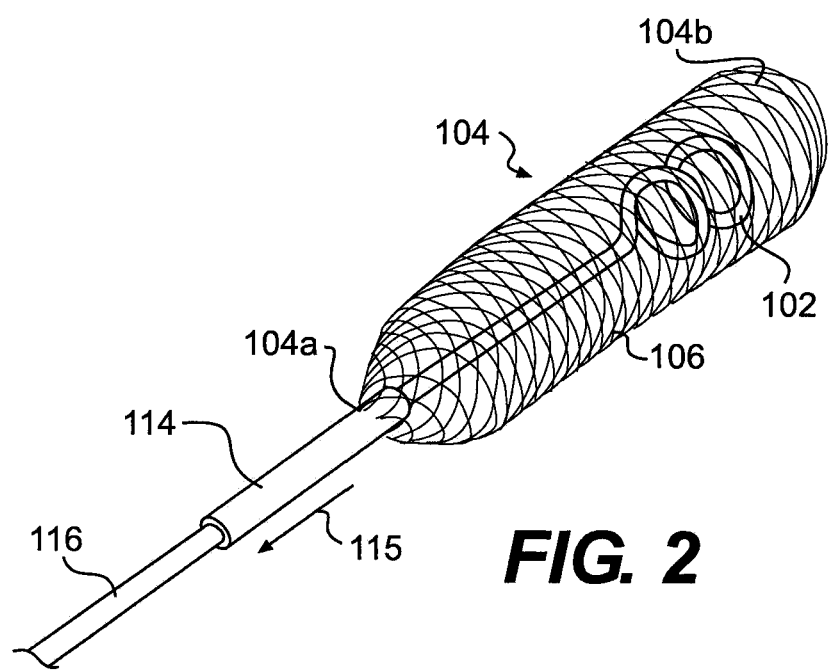
FIG. 2 is a perspective view of a clot capture element and clot engagement element of the medical device of FIG. 1A.
Figure 3A:
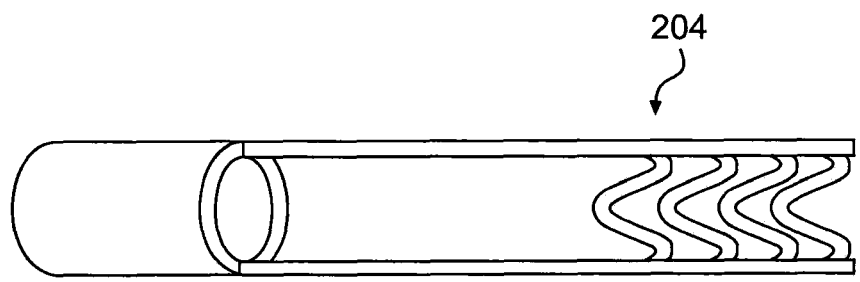
FIGS. 3A-3B are perspective views of a clot capture element, consistent with a second embodiment of the disclosure, in contracted and expanded configurations, respectively.
Figure 3B:
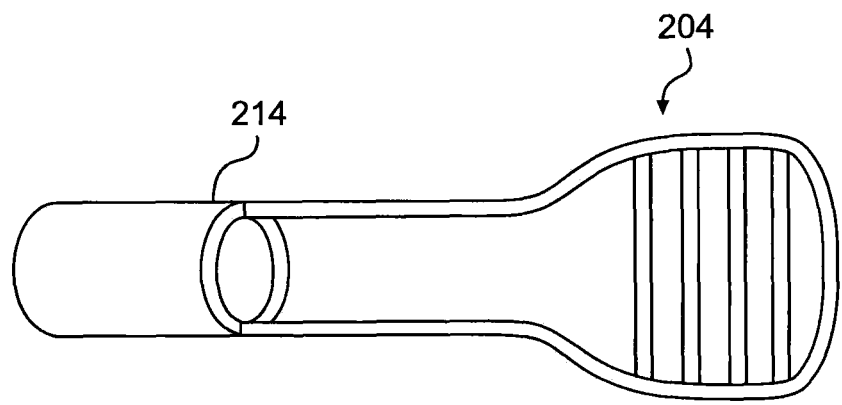

Clot capture element 104 may be any shape and/or configuration such that it may traverse a lumen of a blood vessel. In one embodiment, clot capture element 104 may be a hollow tube having a constant diameter. Alternatively, clot capture element 104 may have a diameter that varies along its length. For example, as illustrated in FIG. 2, clot capture element 104 may have a diameter that tapers at proximal end 104a, such that proximal end 104a may be configured to connect to a distal end of a control shaft 114 (Control shaft 114 will be discussed in further detail below).

Clot capture element 104 may be constructed of any known, suitable biocompatible material having sufficient flexibility and/or rigidity to traverse the lumen of the blood vessel. Biocompatible material of clot capture element 104 may further include properties that may enable clot capture element 104 to expand and contract in the manner previously discussed. Accordingly, biocompatible materials may include, but are not limited to, synthetic plastics, silicone elastomers, thermoplastic elastomers, nickel-titanium, stainless steel, ePTFE, PTFE, polyimides, polyamides, HDPE, polypropylene, polyvinylchloride, LDPE, metal-polymer composites, and metal alloys.

Clot capture element 104 may include a single biocompatible material or a combination of multiple biocompatible materials. In one embodiment, clot capture element 104 may include a variety of biocompatible materials, such that the type and properties of the biocompatible material may vary dependent on the location of the biocompatible material on clot capture element 104. For example, distal end 104b of clot capture element 104 may include materials having spring-like properties. Such biocompatible materials may include, but are not limited to, polyurethanes, low density polyethylene, polyvinylchloride, Nitinol and THV.

It may be desired to have proximal end 104a of clot capture element 104 include a stiffer biocompatible material than that of distal end 104b. The biocompatible material of proximal end 104a of clot capture element 104 may be any suitable degree of stiffness, so long as clot capture element 104 may be configured to traverse a lumen of a blood vessel. Accordingly, the biocompatible materials of proximal end 104a of clot capture element 104 may include, but are not limited to, polyimides, polyamides, high density polyethylene, polypropylene, polyvinylchloride, PTFE, polysulfones, copolymers and blends or mixtures of the aforementioned materials.

Clot capture element 104 may be a unitary structure, formed of a continuous piece of material. Alternatively, as illustrated in FIG. 2, clot capture element 104 may include a multiple components 106. In one embodiment, for example, the multiple components 106 may include a plurality of woven braids intertwined to form a mesh-like structure (FIG. 2). The plurality of woven braids 106 may be connected to one another via any known means. Alternatively, the mesh-like structure may be in the form of a net, and the plurality of woven braids 106 may cross one another without being connected, whereby the plurality of woven braids 106 may be configured to move relative to one another. Additionally, the plurality of woven braids 106 may include a plurality of wires. The wires may be crossed and bent to form the mesh-like structure in a manner such that proximal and distal ends 104a, 104b of clot capture element 104 may be free of open ends of wires (FIG. 2). An absence of open ends may result in reduced trauma to the blood vessel. In other embodiments, free open ends may be used. In some of those embodiments, the open ends may be bent slightly inward or may be otherwise physically structure to minimize vessel trauma.

When a mesh-like structure is employed in the clot capture element 104, the mesh can be constructed in a manner similar to a Chinese finger trap, such that longitudinal retraction forces cause the cylindrical structure to contract radially.

Thus, regardless of other structure that may be employed, one embodiment of the disclosure may simply include a tubular clot capture element, wherein the clot capture element is configured for deployment in a blood vessel for surrounding a clot, the clot capture element having an opening therein configured to receive and guide a clot engaging element, the clot capture element being configured to radially contract upon retraction, such that when the clot capture element surrounds a clot and is retracted in a longitudinal direction of the blood vessel, the clot capture element is configured to exert a radially inward compression force on the clot.

Thus, for example, one embodiment of the disclosure may simply be the structure of capture element 104 in FIG. 2, which has a tubular shape formed of a mesh 106 with an opening 112 at proximal end 104a for receiving and guiding a shaft 116. As the result of its mesh-like structure, upon retraction, the capture element 104 contracts radially inward.

The mesh-like structure can be a net or it can be braided. The net itself might include a plurality of crossing braids such that the crossing braids are movable relative to each other. The net might include a plurality of wires where one or more of the proximal and distal ends of the capture element are free of open ends of wires (see, e.g., distal end of capture element 104 in FIG. 2, where the there are no exposed free ends of wires).

Figure 4A:
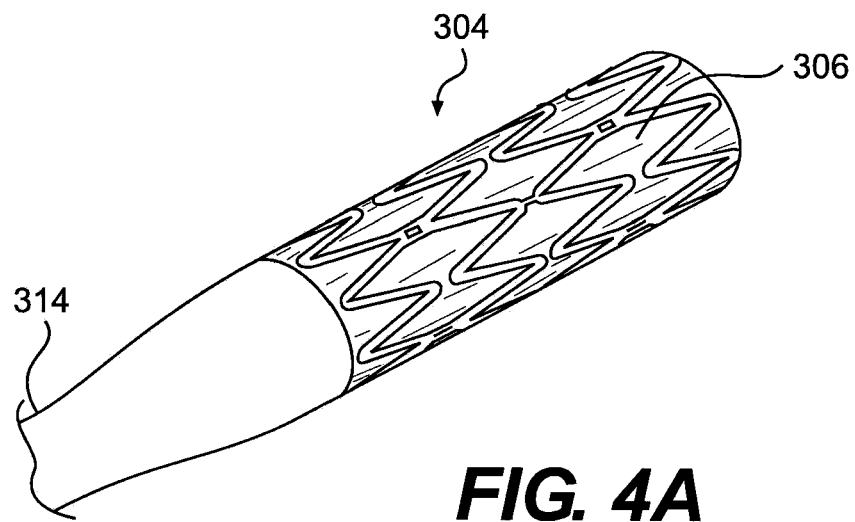
FIGS. 4A-4B are perspective views of a clot capture elements, consistent with third and fourth embodiments of the disclosure, respectively.
Figure 4B:
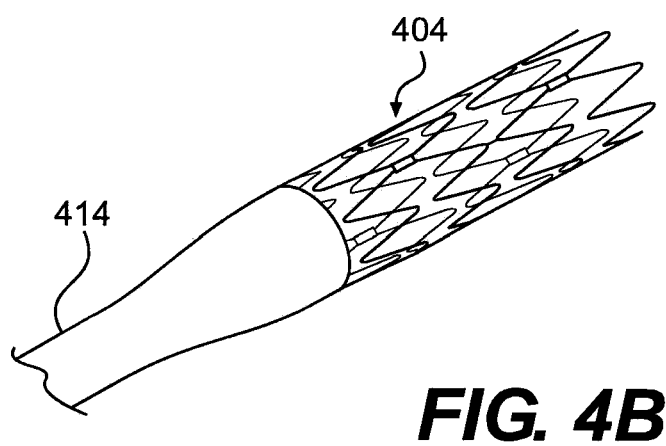

FIGS. 3A-3B and 4A-4B illustrate alternatives to the mesh-like structure, which may include any suitable self-expanding structure. For example, suitable self-expanding structures may include, but are not limited to, rounded coils, flat ribbon coils, a plurality of expandable rings (FIGS. 3A-3B), and/or stent-like structures (FIG. 4A-4B). Self-expanding structures may further be supported between multiple layers of material 306 (e.g., polymers) which may provide suitable structure to clot capture element 104.

Clot capture element 104 may further include an atraumatic exterior surface that may limit tissue damage upon deployment at a clot site. Clot capture element 104 may also include a coating on its exterior and/or interior surfaces. The coating may include an anesthetic and/or a lubricant, which may aid in deployment of clot capture element 104 and clot engagement element 102 and/or may aid in movement of clot engagement element 102 within clot capture element 104.

As noted above, proximal end 104a of clot capture element 104 may be connected to control shaft 114. (See, e.g., FIG. 2) Control shaft 114 may be an elongate member configured to pull clot capture element 104 into the contracted configuration. Elongate member of control shaft 114 may be a hollow tube with a solid wall construction, a braided wall construction, a wound wall construction, a hypo-tube (i.e., solid wall construction with portions removed to facilitate flexing. The hollow tube may have openings on each end such that control shaft 114 may be in communication with central lumen 110 (FIG. 1) of clot capture element 104. Control shaft 114 may thereby allow for passage of tools, including, but not limited to a guidewire 120, and instrumentation for engaging with a clot 1000. Control shaft 114 may further allow for passage of shaft 116 of clot engagement element 102, as illustrated, for example in FIG. 2. Alternatively, control shaft 114 may be of solid construction, and shaft 116 may be positioned adjacent shaft 114, as opposed to running through it.

Shaft 116 may have a diameter that is less than a diameter of control shaft 114, which may allow for clot engagement element 102 to move along a longitudinal axis of clot capture element 104. Shaft 116 may also include a friction minimizing exterior surface. For example, the exterior surface of shaft 116 may be smooth and/or may include a lubricious coating such that shaft 116 may slide with relative ease within control shaft 114. Shaft 116 may further include a lumen therein. The lumen may be in communication with clot capture element 104. The lumen may also be in communication with a lumen 1008 in a blood vessel 1002 when clot removal device 100 is delivered to a clot site. Accordingly, the lumen may allow for insertion of tools useful during a clot removal procedure, including, but not limited to, a guide wire 120, a suction device, illumination devices, imaging devices, and/or suitable instrumentation for grasping a clot.

Control shaft 114 may include a diameter sized to receive shaft 116 in order to allow clot engagement element 102 to be moved within clot capture element 104 through movement of shaft 116. Shaft 116 may have a length that is longer than a length of control shaft 114 (FIG. 2) such that control shaft 114 may at least partially surround shaft 116, which may allow for a device operator to control longitudinal and rotational movement of clot engagement element 102. Control shaft 114 may further be configured to maintain a portion of shaft 116 of clot engagement element 102 in a non-contacting relationship with blood vessel wall 1004 and may be configured to maintain clot engagement element 102 in a desired position relative to clot 1000 at a clot site. Accordingly, control shaft 114 may act as a stabilizer for clot engagement element 102 when clot engagement element 102 is within clot capture element 104. For example, the diameter of control shaft 114 may be large enough to allow for longitudinal and rotational movement of shaft 116, but small enough to prevent shaft 116, and thereby clot engagement element 102, from substantially deviating from a predetermined location relative to clot 1000. Thus, one function of control shaft may be to center shaft 116 within the vessel, such that when engagement element 102 is rotated, the rotation occurs in a substantially longitudinal direction of the vessel.

In the absence of control shaft 114, or in addition to it, centering of the engagement element within the vessel can occur as the result of a tapering of capture element 104, or through the use of a spacer, not shown, for centering shaft 116 in the vessel. In this regard, another embodiment of the disclosure may include a clot removal device, having a shaft, a clot engagement element on an end of the shaft, the clot engagement element and the shaft being configured for deployment in a blood vessel; and a stabilizer configured to at least partially surround the shaft and to maintain a portion of the shaft in a non-contacting relationship with the blood vessel wall.

In FIG. 2, for example, shaft 116 is maintained in non-contacting relationship with the vessel wall through control shaft 114's central interconnection to capture element 104. Thus, when shaft 116 enters the lumen defined by capture element 104, it is biased in a direction toward the center of the vessel. This in turn helps to maintain the engagement element in manner that when rotated, tends to rotate in the longitudinal direction of the vessel rather than substantially transverse to the longitudinal direction. This is just one example of a stabilizer structure. Any structure that holds an engaging element's shaft away from a vessel wall is also contemplated to be encompassed by this embodiment.

Control shaft 114 may also be configured to transition clot capture element 104 from the expanded configuration to an at least partially contracted configuration. For example, movement of control shaft 114 in the direction shown by arrow 115 in FIG. 2 may result in an applied force to proximal end 104a of clot engagement element 104. The applied force to proximal end 104a of clot capture element 104 may also be in the direction shown by arrow 115, which may thereby result in contraction of clot capture element 104.

Figure 7B:
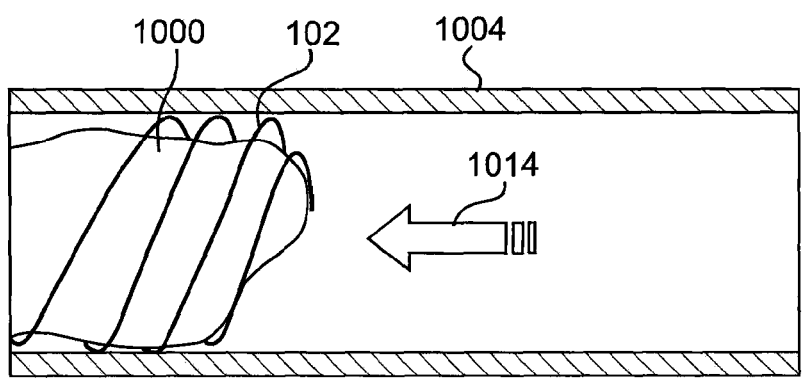
Figure 7C:
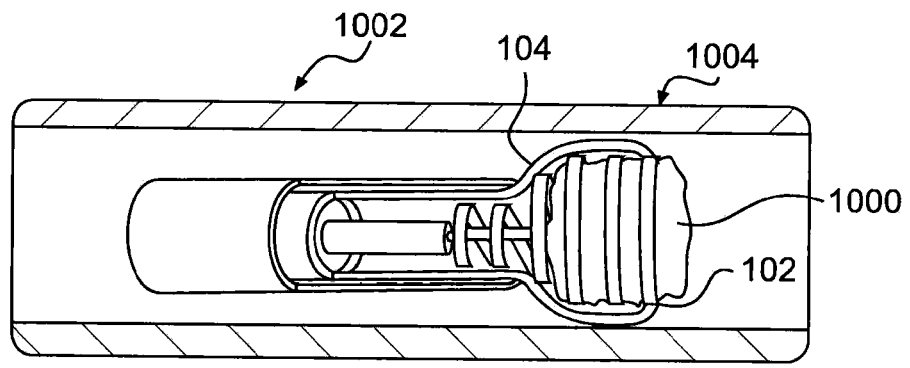
FIGS. 7C-7D are sectional views of the body portion of FIGS. 6A-6B showing steps of removing a clot from the body portion, using the medical device of FIG. 1A.
Figure 7D:
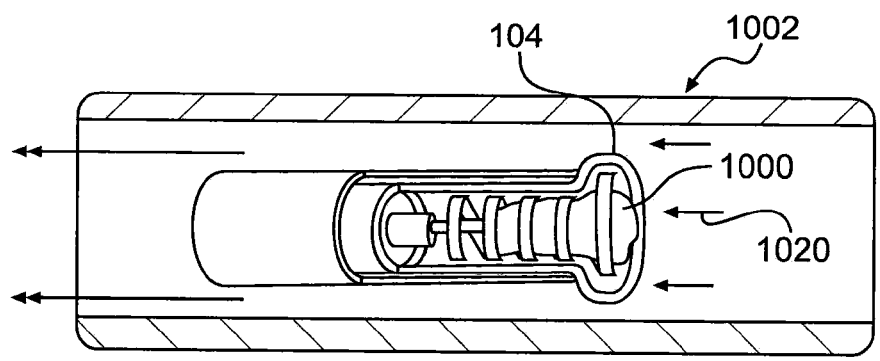
Figure 8:
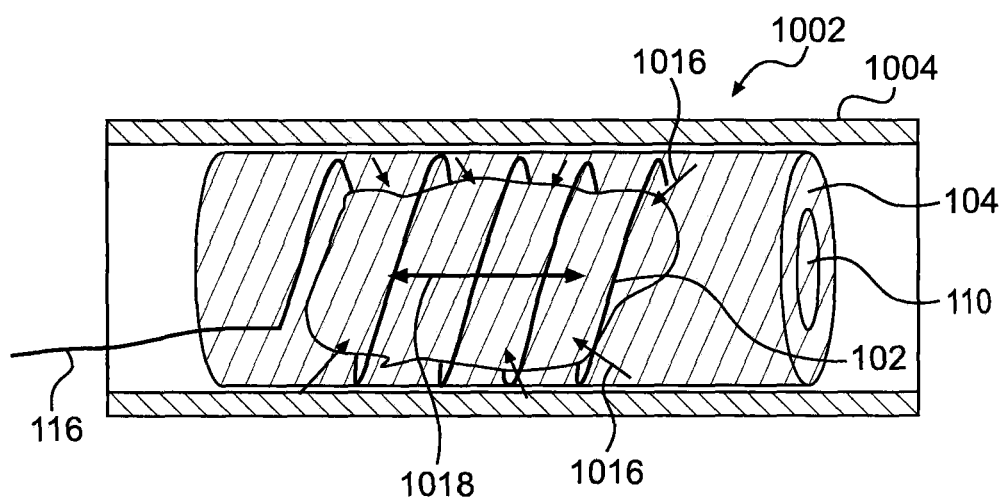
FIG. 8 is a sectional view of the body portion of FIGS. 6A-6B showing forces acting on a clot during a method of removing the clot from the body portion, using the medical device of FIG. 1A.

During retraction, clot capture element 104 may contract, exerting forces 1016, 1018 (FIG. 8) on clot 1000 and/or clot engagement element 102 when clot 1000 and/or clot engagement element 102 are within central lumen 110 of clot capture element. Forces 1016, 1018 may maintain clot 1000 within central lumen 110 of clot capture element 104 during removal of clot 1000 from a blood vessel 1002 and may mitigate a tendency of clot 1000 to break into multiple pieces. The clot may then be retrieved from the vessel with the clot retained solely within the capture element and engagement element, as illustrated in FIGS. 7A and 7B. Alternatively, for clots small enough to fit within sheath 118, the clot can be pulled into the sheath 118 before removal from the vessel, as illustrated in FIGS. 7C and 7D. In this manner, the sheath 118 might exert further holding force on the clot.

In accordance with at least some embodiments, a sheath may be provided, surrounding and compressing the capture element and the engagement element. The sheath may be removable to thereby enable the capture element to expand in a blood vessel in which the sheath is deployed, and to enable the engagement element to expand within the capture element. A sheath may be any structure that is capable of retaining one or more of a clot engaging element and a clot capture element, while being capable of sufficiently flexing in order to deploy one or more of those elements in a vessel.

Consistent with at least some exemplary embodiments of the disclosure, an exemplary sheath 118 is illustrated in FIG. 1. Clot engagement element 102 and clot capture element 104 may be delivered to a clot site within the sheath 118. Sheath 118 may be a hollow tubular structure having a central lumen configured to surround clot engagement element 102 and clot capture element 104 (FIG. 1A). Sheath 118 may further be configured to protect clot engagement element 102 and clot capture element 104 as they follow a delivery path to the clot site. Accordingly, sheath 118 may be made of any suitable biocompatible material and have any suitable shape and/or configuration so long as sheath 118 may be configured to traverse a patient's vasculature while maintaining clot engagement element 102 and clot capture element 104 in their respective contracted configurations upon delivery to and removal from a clot site. Further, upon removal of clot engagement element 102 and clot capture element 104 from the clot site, sheath may be configured to maintain a clot within its central lumen as well (FIG. 7D).

Additionally, sheath 118 may be configured to allow for controlled expansion of clot capture element 104 and clot engagement element 102. For example, as previously discussed, clot capture element 104 and clot engagement element 102 may be configured to expand upon removal of sheath 118. Sheath 118 may be retracted in a direction away from distal end 104b of clot capture element 104. Accordingly, sheath 118 may be removed at a rate that may control the rate of expansion of clot capture element 104 and clot engagement. Further, sheath 118 may be retracted a distance that may control the amount of clot capture element 104 and clot engagement element 102 that may be exposed and expanded (FIG. 1B). Alternatively, the sheath 118 may be help substantially stationary, and the clot capture element 104 and clot engagement element 102 may be advanced, resulting in expansion of those elements.

In accordance with another embodiment of the disclosure there may be provided a tubular clot capture element having a first internal diameter, and a clot engaging element having a second external diameter, wherein the first diameter and the second diameter are selected to permit the clot engaging element to be rotated within the tubular clot capture element.

By way of example only, and as illustrated in FIG. 2 as well as the other figures, the inner diameter of clot capture element 104 is sufficiently sized so that clot engaging element 102 is able to be rotated therein. Depending on the ultimate commercial design, this may provide the operator with the freedom to encircle a clot with an engaging element 102 at the same time that the clot is being drawn into the capture element 104. Or it may provide the operator with the ability to turn the clot once it is within the capture element 104. As such, the elements 102, 104 may be sized such that an outer surface area of the clot engaging element 102 may contact an inner surface area of the clot capture element 104.

Figure 5:
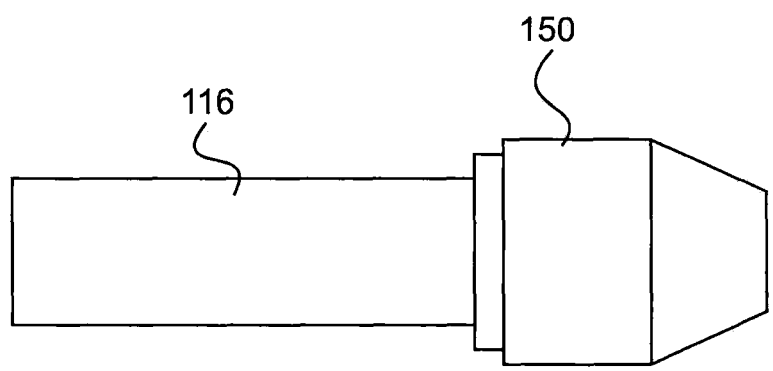
FIG. 5 is a perspective view of a conventional locking mechanism for use with the medical device of FIG. 1A.

During operation of clot removal device 100, a device operator may find it useful to prevent movement of clot engagement element 102 relative to clot capture element 104. This may be desirable, for example, during delivery of clot removal device 100 to the clot site and/or during removal of clot 1000 from a patient. Accordingly, FIG. 5 illustrates a locking mechanism 150 that may be used with clot removal device 100 for selectively locking shaft 116 of clot engagement element 102 in a fixed position with respect to control shaft 114 of clot capture element 104. When locking mechanism 150 is rotated in one direction locking may occur, and when rotated in an opposite direction, release may occur. Locking mechanism may be any suitable device that selectively prevents relative movement between the clot engagement element and the clot capture element. Examples of locking mechanisms may include, but are not limited to, snap locks, rotational locks, and interference fits. For example, in one embodiment, locking mechanism may be a torquer 150. A similar or differing locking mechanism may be used to control relative movement between sheath 118 and capture element 104.

Clot removal device 100 may also include a component that may allow a device operator to know the location of clot removal device 100 as it travels to the clot site. Location components may include, but are not limited to, radiopaque markers, sensors, and/or imaging devices. In one embodiment, for example, distal end 104b of clot capture element 104 may include a radiopaque marker (not shown).

Turning now to FIGS. 6A-6B, 7A-7D, and 8, a procedure of removing a clot from a blood vessel is illustrated using clot removal device 100 shown in FIG. 1A. Clot removal device 100 may be delivered to a clot site within a blood vessel 1002. Delivery of clot removal device 100 may include transporting sheath 118, which may substantially surround clot engagement element 102 and clot capture element 104, within a patient's vasculature to a location proximate a clot 1000. A device operator may insert clot removal device 100 over a guidewire 120 in order to assure clot removal device 100 follows a correct path to the clot site. During delivery within sheath 118, clot engagement element 102 may be substantially surrounded by clot capture element 104, as illustrated in FIG. 1A. Alternatively, clot engagement element 102 may be located outside of clot capture element 104, and may be pulled into clot capture element 102 after grasping clot 1000 during a later point in the procedure.

As previously discussed, a device operator may monitor the location of clot removal device 100 as it approaches the clot site via sensors, radiopaque markers, and/or imaging devices. Once clot removal device 100 has reached the clot site, the device operator may remove guidewire 120 from clot removal device 100. The device operator may retract the sheath 118 (or advance the engagement element) sufficiently so that the engagement element 102 can rotate. Alternatively, the sheath 118 may be removed in its entirety. Upon disassociation of the sheath 118 from clot engagement element 102, clot engagement element 102 may then expand radially and be movable (e.g., longitudinal and rotational movement) within clot capture element 104. Both the clot engaging element 102 and the clot capture element 104 may be self-expanding in a spring-like manner. Clot capture element 104 may expand to the approximate size of the inner diameter of blood vessel 1002. As previously discussed, the expansion of clot capture element 104 may initiate separation of clot 1000 from blood vessel wall 1004.

The device operator may move shaft 116 of clot engagement element 102 in the direction of arrow 1010 towards clot 1000 and rotate shaft 116 in the direction of arrow 1012 which may cause clot engagement element 102 to engage with clot 1000. Longitudinal movement of shaft 116 may cause longitudinal movement of clot engagement element 102 in the direction of arrow 1010', and rotational movement of shaft 116 may cause rotational movement of clot engagement element 102 in the direction of arrow 1012'. Clot engagement element 102 may be moved along a longitudinal axis 1006 of blood vessel towards clot 1000. Upon a distal-most end of clot engaging element 102 reaching clot 1000, simultaneous longitudinal a rotational movement of shaft 116 may cause clot engagement element 102 to encircle clot 1000. If windings 108 of clot capture element 102 have a substantially constant pitch and a substantially constant radius, then as the capture element 102 is wound, the windings will follow a single path, minimizing trauma to the clot, and thereby minimizing risk that the clot will break apart. As clot engagement element 102 encircles clot 1000, clot engagement element 102 may be between clot 1000 and clot capture element. In some instance of use, rotation of clot engagement element 102 might result in an Archimedes screw effect, drawing the clot further into the engagement element 102 without the need to significantly advance the engagement element. The extent of the Archimedes effect, and whether it occurs at all, may vary depending on the specific nature of the clot and the extent of its connection to the vessel wall 1004.

Encircling of clot 1000 by clot engagement element 102 may cause additional expansion of clot engagement element 102. As previously discussed, radially expansion of clot engagement element 102 may cause an outer surface of clot engagement element 102 to exert a force on a wall 1004 of blood vessel 1002, which may further aid in separating clot 1000 from blood vessel wall 1004. The separation may aid in reducing the force needed to remove clot 1000 from blood vessel 1002. The separation may also aid in mitigating the tendency of clot 1000 to break into multiple pieces during removal of the clot from blood vessel 1002.

The device operator may encircle clot 1000 with clot engagement device such that the device operator may be capable of pulling clot engagement element 102 and clot 1000, together, into clot capture element 104. Accordingly, the device operator may move shaft 116 in the direction of arrow 1014 such that clot 1000 encircled by clot engagement element 102 may be pulled through opening 112 and into central lumen 110 of clot capture element 104.

As the device operator pulls clot 1000 and clot engagement element 102 into central lumen 110 of clot capture element 104 in the direction of arrow 1014, the device operator may also pull control shaft 114 of clot capture element 104 in the direction of arrow 115. This pulling may result in clot capture element 104 applying radially contracting forces 1016 and a longitudinal shearing force 1018 to clot 1000 and clot engagement element 102. These applied forces may aid the device operator in maintaining clot 1000 within clot capture element 104 and removing clot 1000 from blood vessel 1002 without breaking clot 1000 into multiple pieces. And if the clot does break, capture element 104 may protect against pieces becoming loose in the bloodstream.

As illustrated in FIG. 7D, the simultaneous pulling of clot capture element 104 and clot 1000 encircled by clot engagement element 102 may result in the aforementioned components being drawn back into sheath 118 in the direction of arrow 1020. The drawing of clot engagement element 102 and clot capture element 104 back into sheath 118, may result in the transition of clot engagement element 102 and clot capture element 104 from the expanded configuration (FIG. 7C) to the contracted configuration (FIG. 7D). The device operator may then remove clot removal device 100 from the patient's vasculature along longitudinal axis 1006 of blood vessel 1002.

Alternatively, the clot may be removed from the vasculature without pulling the capture element and the engaging element back into the sheath. Instead, as the clot may be trapped within the capture element, the radial forces exerted upon retraction may be sufficient to compress the clot within the capture element such that the structure may be retracted in a substantially expanded form.

The device operator may alter the method of removing clot 1000 from blood vessel 1002 as necessary. For example, prior to positioning clot engagement element 102 for encircling of clot 1000, the device operator may insert instrumentation through central lumen of clot capture element 104 which may be necessary for cleaning out the clot site. Additionally, removal of clot 1000 may be accompanied by suitable tools for grasping and/or maintaining clot 1000 within clot capture element 104. For example, the device operator may employ a suctioning device at a proximal end of clot removal device 100. The suctioning device may further aid in pulling clot 1000 into clot capture element 104 and retaining clot 104 within clot capture element 104 as clot 1000 is drawn out of the patient's vasculature.

In accordance with another embodiment of the disclosure, a method of removing a clot from a blood vessel may include deploying a tubular clot capture element in a blood vessel, the clot capture element having an opening therein that receives and guides a clot engaging element, surrounding a clot with the clot capture element, and retracting the clot capture element in a longitudinal direction of the blood vessel, such that the clot capture element radially contracts, exerting a radially inward compression force on the clot. This embodiment of the disclosure may be practiced with any of the clot capture elements described above, including, clot capture element 104.

In accordance with yet another embodiment of the disclosure, a method of removing a clot from a blood vessel may include delivering a tubular clot capture element having a first diameter to a clot site and delivering a clot engaging element having a second external diameter to the clot site, wherein the first diameter and the second diameter are selected to such that the clot engaging element rotates within the tubular clot capture element. As describe earlier in connection with FIG. 2, such a method may be accomplished, for example, when clot capture element 104 is delivered to a clot site, clot engaging element 102 is delivered to a clot site, and when the two elements' diameters permit the engaging element to be rotated within the capture element.

While the capture element and the engaging element may be deployed together, such as in the same sheath, the disclosure in its broadest sense does not necessarily so require. The engaging element may, for example, be delivered first, and the capture element may be subsequently delivered. Moreover, the engaging element when rotated may be sized to contact the inner wall of the capture element, or the engaging element may be sized to avoid contact.

In accordance with a further embodiment of the disclosure, a method for removing a clot from a blood vessel may include deploying a clot engagement element in a blood vessel, the clot engagement element located on an end of a shaft; and at least partially surrounding the shaft with a stabilizer to maintain a portion of the shaft in a non-contacting relationship with the blood vessel wall. This method may be practiced with or without a clot capture element, such as structure 104, and without regard to any specific stabilizing structure. As was previously noted, depending on design choice, some embodiments of the disclosure may benefit from a rotation of the engagement element 102 when the engagement element is centered in the vessel. This may minimize the pressure exerted on the vessel walls, while maximizing movement of the engagement element 102 in the longitudinal direction of the vessel to surround the clot. By stabilizing, toward the center of the vessel, the shaft (e.g., shaft 116) that rotates the engagement element (e.g., 102), longitudinal motion may be maximized. Thus, stabilization may occur by surrounding shaft 116 with any structure that generally maintains it near the center of the vessel at locations proximate the intersection of shaft 116 and windings 108.

Other embodiments of the disclosure will be apparent to those skilled in the art from consideration of the specification and practice of the invention disclosed herein. It is intended that the specification and examples be considered as exemplary only, with a true scope and spirit of the disclosure being indicated by the following claims.

What is claimed is:

1. A clot removal device configured for deployment from a proximal side of a clot location, the device comprising:
    an expandable clot capture element configured for deployment to the clot location from the proximal side;
    an expandable clot engagement element including a helix and configured for deployment to the clot location from the proximal side while compressed in a substantially non-expanded state within the clot capture element, and wherein the helix has an open end on a distal side thereof configured, in an expanded state, to encircle a clot from the proximal side of the clot location, with a terminal end of the clot engagement element being located substantially at the expanded open end of the helix and aligned with a circumference of the helix, to define a substantially unobstructed channel for encircling the clot; and
    a sheath surrounding and compressing the capture element and the engagement element in a pre-deployed state, wherein the capture element and the engagement element are simultaneously compressed within the sheath prior to clot encirclement, the sheath being removable upon deployment to enable the engagement element to expand within the capture element on the proximal side of the clot location prior to clot encirclement.

2. The device of claim 1, wherein the capture element surrounds the engagement element.

3. The device of claim 1, wherein the engagement element is a coil.

4. The device of claim 1, wherein the engagement element is sized to be movable within the capture element upon removal of the sheath.

5. The device of claim 1, wherein the engagement element is sized to be rotatable within the capture element upon removal of the sheath.

6. The device of claim 1, wherein the capture element has a length that is longer than a length of the engagement element.

7. The device of claim 1, further comprising a locking mechanism for locking the clot engagement element within the clot capture element.

8. The device of claim 1, wherein the capture element is sized so that in a deployed state it engages a blood vessel wall, and wherein the engagement element is sized so that in a deployed state the engagement element is movable within the capture element.

9. The device of claim 1, wherein the capture element and the engagement element are configured such that when used, the engagement element is between the capture element and the clot.

10. The device of claim 1, wherein the helix, in an expanded state, is configured to exhibit a substantially constant radius.

11. The device of claim 1, wherein the helix, in an expanded state, is configured to exhibit a substantially constant pitch.

12. The device of claim 1, wherein the helix is configured for rotation to thereby encircle the clot from the proximal side of the clot location.

13. The device of claim 1, wherein the clot capture element is configured for positioning proximal to the clot engagement element and is sized to enable the encircled clot to be pulled proximally into the clot capture element.

14. The device of claim 1, wherein the capture element and the engagement element are configured such that when used, the engagement element is between the capture element and the clot.

* * * * *